(12) United States Patent
Fotos et al.

(10) Patent No.: US 6,214,402 B1
(45) Date of Patent: Apr. 10, 2001

(54) CO-CRYSTALLIZATION OF SUGAR AND N-[N-(3,3-DIMETHYLBUTYL)-L αASPARTYL]-L-PHENYLALANINE 1-METHYL ESTER

(75) Inventors: Jim Fotos, Wheeling; Ihab E. Bishay, Mundelein; Indra Prakash, Hoffman Estates; Kurt Wachholder, Elgin; Nitin Desai, Mount Prospect, all of IL (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 09/154,568

(22) Filed: Sep. 17, 1998

(51) Int. Cl.$^7$ ................................................. A23L 1/236
(52) U.S. Cl. ..................... 426/548; 426/549; 426/590; 426/658; 560/40
(58) Field of Search ........................... 426/548, 549, 426/590, 650, 658; 560/40

(56) References Cited

U.S. PATENT DOCUMENTS

| 4,031,258 | * | 6/1977 | Haas et al. ........................... 426/548 |
| 4,153,737 | * | 5/1979 | Berg et al. ........................... 426/548 |
| 4,362,757 | | 12/1982 | Chen ..................................... 426/599 |
| 5,480,668 | | 1/1996 | Nofre ..................................... 426/548 |
| 5,510,508 | | 4/1996 | Claude .................................. 560/41 |
| 5,728,862 | | 3/1998 | Prakash ................................ 560/40 |

FOREIGN PATENT DOCUMENTS

99/30576   6/1999   (WO).

OTHER PUBLICATIONS

Patent Abstracts of Japan, vol. 009, No. 260 (C–309), Oct. 17, 1985 (corresponds to JP 60–114169).
Patent Abstracts of Japan, vol. 008, No. 162 (C–235), Jul. 26, 1984 (corresponds to JP 59–063158).

* cited by examiner

*Primary Examiner*—Leslie Wong
(74) *Attorney, Agent, or Firm*—Fitzpatrick, Cella, Harper & Scinto

(57) ABSTRACT

This disclosure relates to the co-crystallization of N-[N-(3,3-dimethylbutyl)-L-α-aspartyl]-L-phenylalanine 1-methyl ester with sugar in various ratios. The sugar co-crystallized sweetener is very soluble in water and has no dusting problems.

19 Claims, No Drawings

CO-CRYSTALLIZATION OF SUGAR AND N-[N-(3,3-DIMETHYLBUTYL)-L αASPARTYL]-L-PHENYLALANINE 1-METHYL ESTER

BACKGROUND OF THE INVENTION

1. Field of the Invention

This invention relates to a water-soluble, non-dusting, sugar co-crystallized N-[N-(3,3-dimethylbutyl)-L-α-aspartyl]-L-phenylalanine 1-methyl ester (neotame) composition. This invention also relates to a process for producing a water-soluble, non-dusting sugar co-crystallized neotame composition, as well as to beverages, fluid dairy products, condiments, baked goods, frostings, bakery fillings, candy, chewing gum or table-top sweeteners prepared with the sugar co-crystallized N-[N-(3,3-dimethylbutyl)-L-α-aspartyl]-L-phenylalanine 1-methyl ester compositions and methods of preparing the same.

2. Related Background Art

U.S. Pat. No. 4,362,757 describes a crystallized sugar product containing a heat-sensitive, acidic, or high invert sugar substance. Such crystallized sugar products are said to be dry, granular, free-flowing, non-caking and readily dispersible in water. The crystallized sugar products are formed via a two-step process: preparing a premix of dry granular or transformed sugar base with a heat-sensitive, acidic or high invert sugar substance; and then co-crystallizing by concentrating a sugar syrup, adding a predetermined amount of premix and subjecting the mixture to impact beating.

The use of high potency dipeptide sweeteners, such as neotame (about 8000× sweeter than sucrose), requires consideration of the ability to deliver the sweetener and the solubility of the sweetener. Thus, effective means for delivering such a high potency sweetener such as neotame in desired compositions would be very useful. In particular, it is highly desirable to provide a means for uniformly dispersing a high potency dipeptide sweetener such as neotame so as to avoid "hot spots" of high intensity sweetener.

SUMMARY OF THE INVENTION

This invention relates to the co-crystallization of N-[N-(3,3-dimethylbutyl)-L-α-aspartyl]-L-phenylalanine 1-methyl ester with sugar in various ratios resulting in increased solubility and enhanced delivery characteristics. In addition, the products of this invention provide for the uniform dispersion of neotame in any application, thus avoiding "hot spots".

The sugar co-crystallized sweetener composition of this invention comprises sugar and N-[N-(3,3-dimethylbutyl)-L-α-aspartyl]-L-phenylalanine 1-methyl ester. The composition of this invention can be used, for example, as a sweetener for incorporation in processed foods and beverages or as a table-top sweetener.

In a preferred embodiment of the sugar co-crystallized sweetener composition of the present invention, the N-[N-(3,3-dimethylbutyl)-L-α-aspartyl]-L-phenylalanine 1-methyl ester is present in an amount from 0.001% to 50% by weight of the final product. More preferably this range is from 0.001% to 5%, and most preferably this range is from 0.001% to 2.5%.

Without being bound to theory, it is believed that the sugar co-crystallized sweetener composition may comprise agglomerates.

In yet another preferred embodiment of this invention, the sugar co-crystallized N-[N-(3,3-dimethylbutyl)-L-α-aspartyl]-L-phenylalanine 1-methyl ester composition additionally comprises another sweetener, which is selected from a natural sweetener, a high intensity sweetener, or a mixture thereof.

The present invention is also directed to a process for preparing a sugar co-crystallized sweetener composition comprising the steps of mixing sugar with water with agitation, heating the resultant mixture to about 120° C., seeding the mixture with a premix comprised of N-[N-(3,3-dimethylbutyl)-L-α-aspartyl]-L-phenylalanine 1-methyl ester and sugar, removing the mixture from the heat and allowing the mixture to cool with vigorous agitation.

The present invention is also directed to a method of sweetening beverage, dessert, condiment, candy, chewing gum and table-top sweetener compositions by adding a sugar co-crystallized N-[N-(3,3-dimethylbutyl)-L-α-aspartyl]-L-phenylalanine 1-methyl ester composition in an amount effective to sweeten such a composition.

This invention is also directed to compositions such as beverages, fluid dairy products, condiments, baked goods, frostings, bakery fillings, candy and chewing gum containing the sugar co-crystallized sweetener composition of this invention in an amount effective to sweeten the compositions.

The invention also includes table-top sweeteners comprised of the sugar co-crystallized N-[N-(3,3-dimethylbutyl)-L-α-aspartyl]-L-phenylalanine 1-methyl ester composition of this invention.

DETAILED DESCRIPTION

The sugar used in the present invention is sucrose of formula, $C_{12}H_{22}O_{11}$. For purposes of this invention, the term "sugar" is used to refer to sucrose in its dry or syrup form.

The N-[N-(3,3-dimethylbutyl)-L-α-aspartyl]-L-phenylalanine 1-methyl ester used in the present invention has the formula

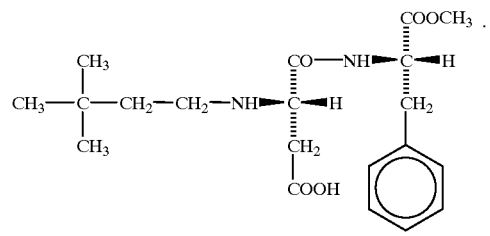

Salts and complexes of neotame are also suitable for use in the present invention.

The N-[N-(3,3-dimethylbutyl)-L-α-aspartyl]-L-phenylalanine 1-methyl ester may be prepared through a variety of methods. One such method comprises the steps of (i) treating a mixture of aspartame and 3,3-dimethylbutyraldehyde in an organic solvent with hydrogen in the presence of a hydrogenation catalyst at a temperature and pressure effective to form an organic solvent solution of N-[N-(3,3-dimethylbutyl)-L-α-aspartyl]-L-phenylalanine 1-methyl ester; (ii) filtering the organic solvent solution to remove the hydrogenation catalyst; and (iii) forming an aqueous/organic solvent solution from the organic solvent solution to precipitate the N-[N-(3,3-dimethylbutyl)-L-α-aspartyl]-L-phenylalanine 1-methyl ester from the aqueous/organic solvent solution. Preferably, the aqueous/organic solvent solution has an amount of organic solvent of about 17% to about 30% by weight of the aqueous/organic solvent solution. A particularly preferred organic solvent for use in this method is methanol. The precipitate is recovered using standard filtration techniques to provide highly purified N-[N-3,3-dimethylbutyl)-L-α-aspartyl]-L-phenylalanine 1-methyl ester. This method of preparation is described in U.S. Pat. No. 5,728,862, the entire disclosure of which is incorporated by reference herein. Further, the entire disclosures of U.S. Pat. Nos. 5,480,668 and 5,510,508, also related to the synthesis and purification of N-[N-(3,3-dimethylbutyl)-L-α-aspartyl]-L-phenylalanine 1-methyl ester, are incorporated by reference herein.

One aspect of the present invention is a process for preparing a sugar co-crystallized N-[N-(3,3-dimethylbutyl)-L-α-aspartyl]-L-phenylalanine 1-methyl ester composition. In the first step of this process, a sugar syrup is obtained. This can be accomplished by obtaining a commercially available sugar syrup or by mixing sugar with water with agitation. Agitation can be provided by any conventional means. Typically, a sugar syrup which is about 67% sucrose and 33% water is commercially available. However, other sugar syrups with different sucrose concentrations may also be used for purposes of the present invention.

In the second step of the process, water is removed to produce a supersaturated sugar syrup. This is most readily accomplished through heating the syrup with agitation, though any conventional method would suffice. The resulting syrup is maintained at a temperature not less than about 120° C. in order to prevent premature crystallization. The solids content of the resulting syrup is from 95–98% by weight of the syrup.

A dry premix comprising N-[N-(3,3-dimethylbutyl)-L-α-aspartyl]-L-phenylalanine 1-methyl ester or salt thereof and sugar is prepared. The weight ratio of neotame to sugar in this premix ranges from about 0.001:1 to about 1:1. Other components, such as flavors or other high potency sweeteners in extremely small amounts, may be added in this step, so long as the amount added does not adversely affect the overall taste of the sugar co-crystallized sweetener composition.

In the next step of the process of the present invention, a predetermined amount of the premix is added to the syrup with vigorous mechanical agitation or impact beating within a suitable crystallization zone, such as a Hobart Mixer or Turbulizer. Alternatively, the concentrated syrup may be added to a predetermined amount of the premix and mixed in a similar manner. The amount of premix added can be varied in order to result in final products with varying N-[N-(3,3-dimethylbutyl)-L-α-aspartyl]-L-phenylalanine 1-methyl ester content. In a preferred embodiment of the present invention, the N-[N-(3,3-dimethylbutyl)-L-α-aspartyl]-L-phenylalanine 1-methyl ester sweetener is present in an amount from 0.001% to 50% by weight of the final product. More preferably this range is from 0.001% to 5%, and most preferably this range is from about 0.001% to 2.5%.

After addition of the premix, the sugar syrup is removed from the heat. During crystallization, it is desirable to remove the heat of crystallization to prevent overheating within the crystallization zone. The heat of crystallization can be removed or dissipated by indirect heat exchange, e.g., by surrounding the crystallization zone with a water jacket, or preferably, by forced air flow through the beater-crystallizer, e.g. with a vapor separator.

The mixture is then cooled quickly with vigorous agitation. Agitation is continued until the mixture is transformed, crystallized and agglomerated. When the mixture reaches the relatively dry agglomerated state, the resulting product is a homogeneous blend of the co-crystallized sugar and N-[N-(3,3-dimethylbutyl)-L-α-aspartyl]-L-phenylalanine 1-methyl ester.

The latent heat of crystallization is generally sufficient to evaporate the moisture so the sugar co-crystallized N-[N-(3,3-dimethylbutyl)-L-α-aspartyl]-L-phenylalanine 1-methyl ester composition is substantially dry. If desired, the sugar co-crystallized sweetener composition may be further dried.

The physical structure of the sugar co-crystallized N-[N-(3,3-dimethylbutyl)-L-α-aspartyl]-L-phenylalanine 1-methyl ester composition is highly dependent on the rate and temperature of agitation and crystallization, and on the degree of sugar transformation. Generally, the less time the mixture spends at high temperature the better. N-[N-(3,3-dimethylbutyl)-L-α-aspartyl]-L-phenylalanine 1-methyl ester sweetener tends to degrade if maintained at a high temperature for a prolonged period of time.

The sugar co-crystallized N-[N-(3,3-dimethylbutyl)-L-α-aspartyl]-L-phenylalanine 1-methyl ester compositions of the present invention are generally in the form of aggregates or agglomerates of sucrose crystals intimately associated with the N-[N-(3,3-dimethylbutyl)-L-α-aspartyl]-L-phenylalanine 1-methyl ester sweeteners. The agglomerates form a loose, lacy network bonded together at their interfaces by point contact. Accordingly, aqueous liquid can rapidly penetrate the porous cluster of agglomerates and free each of the particles making up the agglomerates. The particles thus become readily dispersed and/or dissolved in the aqueous liquid.

In the sugar co-crystallized N-[N-(3,3-dimethylbutyl)-L-α-aspartyl]-L-phenylalanine 1-methyl ester composition of the present invention, the N-[N-(3,3-dimethylbutyl)-L-α-aspartyl]-L-phenylalanine 1-methyl ester sweetener is incorporated as an integral part of the sugar matrix and there is no tendency for the N-[N-(3,3-dimethylbutyl)-L-α-aspartyl]-L-phenylalanine 1-methyl ester sweetener to separate or settle out during handling, packaging or storage. The resulting product is granular, free-flowing, non-caking and is readily and uniformly dispersed or dissolved in water.

The sugar co-crystallized N-[N-(3,3-dimethylbutyl)-L-α-aspartyl]-L-phenylalanine 1-methyl ester compositions of this invention are suitable for use in any food to replace natural sweeteners, as well as other high intensity sweeteners, normally used as sweeteners. The term food as used herein includes, for example, beverages, fluid dairy products, condiments, baked goods, frostings, bakery fillings, candy and chewing gum.

Beverages include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tea-leaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra high temperature, ohmic heating or commercial aseptic sterilization) and hot-filled packaging; and cold-filled products made through filtration or other preservation techniques.

Fluid dairy products include, without limitation, non-frozen, partially frozen and frozen fluid dairy products such as, for example, milks, ice creams, sorbets and yogurts.

Condiments include, without limitation, ketchup, mayonnaise, salad dressing, Worcestershire sauce, fruit-flavored sauce, chocolate sauce, tomato sauce, chili sauce, and mustard.

Baked goods include, without limitation, cakes, cookies, pastries, breads, donuts and the like.

Bakery fillings include, without limitation, low or neutral pH fillings, high, medium or low solids fillings, fruit or milk based (pudding type or mousse type) fillings, hot or cold make-up fillings and non-fat to full-fat fillings.

This invention is also directed to a sweetened food composition, such as described above, containing an effective amount of the sugar co-crystallized N-[N-(3,3-dimethylbutyl)-L-$\alpha$-aspartyl]-L-phenylalanine 1-methyl ester composition of this invention to sweeten the food composition. Determination of the amount of sugar co-crystallized N-[N-(3,3-dimethylbutyl)-L-$\alpha$-aspartyl]-L-phenylalanine 1-methyl ester composition to be added to the food composition can be readily determined by one of ordinary skill in the art.

The sugar co-crystallized sweetener composition of the present invention can be used for this purpose alone or in combination with known bulking agents. Suitable bulking agents include, but are not limited to, dextrose, maltodextrin, lactose, inulin, polyols, polydextrose, cellulose and cellulose derivatives and organic acids including, but not limited to, citric acid and malic acid. Such a product may be suitable for use especially for table-top sweeteners and powdered soft drinks. A table-top sweetener comprising the present sugar co-crystallized sweetener composition may also include any other ingredients commonly present in table-top sweeteners in order to tailor the taste of the product to a specific end use. A table-top sweetener comprising the present sugar co-crystallized sweetener composition may take any known form. Suitable forms include, but are not limited to, sachets including the sweetener in powder or granular form, tablets, liquid sweeteners, and jar, pouches, pocket or other forms in which the sweetener may be measured in, for example, spoon for spoon form.

The sugar co-crystallized N-[N-(3,3-dimethylbutyl)-L-$\alpha$-aspartyl]-L-phenylalanine 1-methyl ester compositions of this invention can also include known natural sweeteners as well as other high intensity sweeteners. Sweeteners that may be employed include, without limitation, aspartame, acesulfame-K, sucralose, saccharin, alitame, cyclamates, stevia derivatives, thaumatin, sucrose (liquid and granulated), high fructose corn syrup, high conversion corn syrup, crystalline fructose, glucose (dextrose), polyol sugar alcohols, invert sugar and mixtures thereof.

The Examples which follow are intended as an illustration of certain preferred embodiments of the invention, and no limitation of the invention is implied.

EXAMPLE 1

0.25% N-[N-(3,3-dimethylbutyl)-L-$\alpha$-aspartyl]-L-phenylalanine 1-methyl ester (neotame)

150.0 g sucrose and 30.0 g water were mixed on a Dispermat. The solution was heated to 108° C., with an additional 10.0 g water being added after 13 minutes. The solution was removed from the heat. The solution was seeded with 0.3929 g neotame and 5.0 g sucrose dry mixed together. The mixture was removed from the Dispermat and transferred to the Hobart mixer for further mixing for 2 minutes. The resulting product was a sugar co-crystallized neotame composition.

EXAMPLE 2

0.1125% N-[N-(3,3-dimethylbutyl)-L-$\alpha$-aspartyl]-L-phenylalanine 1-methyl ester (neotame)

195.0 g sucrose and 100.0 g water were mixed on a Dispermat. The solution was heated to 125° C. The solution was removed from the heat. The solution was seeded with 0.2250 g neotame and 5.0 g sucrose dry mixed together. The mixture frothed up. The mixture was removed from the Dispermat and transferred to a Hobart mixer to break up clumps for 2 minutes. The resulting product was a sugar co-crystallized neotame composition.

EXAMPLE 3

0.0125% N-[N-(3,3-dimethylbutyl)-L-$\alpha$-aspartyl]-L-phenylalanine 1-methyl ester (neotame)

195.0 g sucrose and 100.0 g water were mixed on a Dispermat. The solution was heated to 123° C. The solution was removed from the heat. The solution was seeded with 0.0250 g neotame and 5.0 g sucrose dry mixed together. The mixture frothed up. The mixture was removed from the Dispermat and transferred to a Hobart mixer to break up clumps for 2 minutes. The resulting product was a sugar co-crystallized neotame composition.

EXAMPLE 4

2.4% N-[N-(3,3-dimethylbutyl)-L-$\alpha$-aspartyl]-L-phenylalanine 1-methyl ester (neotame)

195.0 g sucrose and 100.0 g water were mixed on a Dispermat. The solution was heated to 123° C. The solution was removed from the heat. The solution was seeded with 5.0 g neotame and 5.0 g sucrose dry mixed together. The mixture was removed from the Dispermat and transferred to a Hobart mixer for further mixing for 2 minutes. The resulting product was a sugar co-crystallized neotame composition.

COMPARATIVE EXAMPLE 1

Crystallized Sugar Syrup 350.0 g sucrose and 40.0 g water were mixed and heated to 115° C. The solution was removed from the heat and mixed with a Dispermat. Finally, the mixture was transferred to a Hobart mixer for further agitation.

Uniformity

Samples 1–3 were sampled from the material prepared according to Example 1. Samples 4–6 were sampled from the material prepared according to Example 2. Samples 7–9 were sampled from the material prepared according to Example 3. Samples 10–12 were sampled from the material prepared according to Example 4.

TABLE 1

| sample | theoretical neotame wt/wt % | experimental assay neotame wt/wt % | main degradant wt/wt % |
|---|---|---|---|
| 1 | 0.2500 | 0.21435 | 0.00065 |
| 2 | 0.2500 | 0.21631 | 0.00063 |
| 3 | 0.2500 | 0.21251 | 0.00066 |

TABLE 1-continued

| sample | theoretical neotame wt/wt % | experimental assay neotame wt/wt % | main degradant wt/wt % |
|---|---|---|---|
| 4 | 0.1125 | 0.09204 | 0.00115 |
| 5 | 0.1125 | 0.09182 | 0.00115 |
| 6 | 0.1125 | 0.09200 | 0.00113 |
| 7 | 0.0125 | 0.00982 | no result |
| 8 | 0.0125 | 0.00988 | 0.00020 |
| 9 | 0.0125 | 0.00994 | 0.00022 |
| 10 | 2.4390 | 1.71555 | 0.01608 |
| 11 | 2.4390 | 1.72854 | 0.01587 |
| 12 | 2.4390 | 1.68486 | 0.01529 |

TABLE 2

| uniformity results | theor. 0.2500% wt/wt % | theor. 0.1125% wt/wt % | theor. 0.0125% wt/wt % | theor. 2.4390% wt/wt % |
|---|---|---|---|---|
| average experimental assay | 0.21439 | 0.09195 | 0.00988 | 1.70965 |
| standard deviation | 0.0019 | 0.0001 | 0.0001 | 0.0224 |

The above results demonstrate that neotame mixes in liquid state with sucrose with good uniformity at low levels.

Taste Profile 1

The sugar co-crystallized neotame compositions prepared above were dissolved in water at a concentration to deliver 6 ppm neotame and compared to a solution of crystallized sugar with 0% neotame.

TABLE 3

| sample | Sample Identification: |
|---|---|
| 1S | water solution of sugar co-crystallized with 0.0125% neotame |
| 2S | water solution of sugar co-crystallized with 0.1125% neotame |
| 3S | water solution of sugar co-crystallized with 0.25% neotame |
| 4S | water solution of sugar co-crystallized with 2.5% neotame |
| Comp. 1S | water solution of 6% sugar with 0% neotame |

The samples were prepared and kept refrigerated prior to tasting. The samples were at room temperature when served.

The samples were tasted by a trained test panel. The results of the taste testing indicate that the sugar co-crystallized N-[N-(3,3-dimethylbutyl)-L-α-aspartyl]-L-phenylalanine 1-methyl ester compositions of the present invention are substantially similar with respect to taste profile as compared to pure sucrose.

Taste Profile 2

The flavor profile of samples of co-crystallized sugar with neotame at varying ratios were compared to the flavor profiles of dry blends of neotame and sugar in the same ratios.

TABLE 4

| sample | Sample Identification. |
|---|---|
| | DRY BLENDS |
| 1 | 25% neotame/75% sucrose (1.40 ppm neotame/5.3404% sucrose) |
| 2 | 50% neotame/50% sucrose (3.30 ppm neotame/3.213% sucrose) |
| 3 | 75% neotame/25% sucrose (6.05 ppm neotame/1.085% sucrose) |
| | CO-CRYSTALLIZED BLENDS |
| 4 | 25% neotame/75% sucrose (weigh 53.4054 g for 1000 mL batch) |
| 5 | 50% neotame/50% sucrose (weigh 32.3163 g for 1000 mL batch) |
| 6 | 75% neotame/25% sucrose (weigh 10.8560 g for 1000 mL batch) |

\* Percentages indicate sweetness contribution and not solids content.

The dry blended samples were prepared by weighing the appropriate amount of sucrose and mixing thoroughly with the corresponding volume of neotame stock solution (at 20 ppm) and room temperature water.

The co-crystallized samples were prepared by weighing the appropriate amount of dry solids and mixing with room temperature water until thoroughly dissolved. The co-crystallized samples were processed to deliver the same ratio of ppm neotame/% sucrose per blend as in the dry blended samples.

The samples were tasted by a trained test panel. The results of the taste testing indicate that tastes of the co-crystallized N-[N-(3,3-dimethylbutyl)-L-α-aspartyl]-L-phenylalanine 1-methyl ester samples were very similar to the profiles of the dry blended samples at all three ratios tested.

Other variations and modifications of this invention will be obvious to those skilled in this art. This invention is not to be limited except as set forth in the following claims.

What is claimed is:

1. A process for preparing a sugar co-crystallized sweetener composition comprising the steps of:

(a) mixing sugar with water with agitation to form a mixture;

(b) heating said mixture to approximately 120° C.;

(c) seeding said mixture with a premix comprised of N-[N-(3,3-dimethylbutyl)-L-α-aspartyl]-L-phenylalanine 1-methyl ester or salt thereof and sugar;

(d) removing said mixture from the heat; and (e) allowing the mixture to cool with vigorous agitation.

2. The process for preparing a sugar co-crystallized sweetener composition according to claim 1, wherein the weight ratio of N-[N-(3,3-dimethylbutyl)-L-α-aspartyl]-L-phenylalanine 1-methyl ester to sugar in said premix is from about 0.001:1 to about 1:1.

3. The process for preparing a sugar co-crystallized sweetener composition according to claim 1, wherein the amount of N-[N-(3,3-dimethylbutyl)-L-α-aspartyl]-L-phenylalanine 1-methyl ester and sugar in a final product is from 0.001% to 50% by weight.

4. The process for preparing a sugar co-crystallized sweetener composition according to claim 3, wherein the amount of N-[N-(3,3-dimethylbutyl)-L-α-aspartyl]-L-phenylalanine 1-methyl ester and sugar in a final product is from 0.001% to 5% by weight.

5. The process for preparing a sugar co-crystallized sweetener composition according to claim 4, wherein the amount of N-[N-(3,3-dimethylbutyl)-L-α-aspartyl]-L-phenylalanine 1-methyl ester and sugar in a final product is from 0.001% to 2.5% by weight.

6. The process for preparing a sugar co-crystallized sweetener composition according to claim 1, wherein said composition is comprised of agglomerates.

7. A method of sweetening a beverage by including in said beverage a sugar co-crystallized sweetener composition comprising sugar and N-[N-(3,3-dimethylbutyl)-L-α-aspartyl]-L-phenylalanine 1-methyl ester or a salt thereof in an amount effective to sweeten said beverage.

8. The method according to claim 7, wherein said beverage is selected from the group consisting of carbonated soft drinks, powdered soft drinks, coffees, teas, juices, sweetened and flavored waters, sport/energy/health drinks, alcoholic beverages, beverages processed with heating and hot-filled packaging and cold-filled beverages.

9. A method of sweetening a fluid dairy product by including in said fluid dairy product a sugar co-crystallized sweetener composition comprising sugar and N-[N-(3,3-dimethylbutyl)-L-α-aspartyl]-L-phenylalanine 1-methyl ester or a salt thereof in an amount effective to sweeten said fluid dairy product.

10. The method according to claim 9, wherein said fluid dairy product is selected from the group consisting of non-frozen, partially frozen and frozen milks, ice creams, sorbets and yogurts.

11. A method of sweetening a condiment by including in said condiment a sugar co-crystallized sweetener composition comprising sugar and N-[N-(3,3-dimethylbutyl)-L-α-aspartyl]-L-phenylalanine 1-methyl ester or a salt thereof in an amount effective to sweeten said condiment.

12. The method according to claim 11, wherein said condiment is selected from the group consisting of ketchup, mayonnaise, salad dressing, Worcestershire sauce, tomato sauce, chili sauce, and mustard.

13. A method of sweetening a baked good by including in said baked good a sugar co-crystallized sweetener composition comprising sugar and N-[N-(3,3-dimethylbutyl)-L-α-aspartyl]-L-phenylalanine 1-methyl ester or a salt thereof in an amount effective to sweeten said baked good.

14. The method according to claim 13, wherein said baked good is selected from the group consisting of cakes, cookies, pastries, breads and donuts.

15. A method of sweetening a frosting by including in said frosting a sugar co-crystallized sweetener composition comprising sugar and N-[N-(3,3-dimethylbutyl)-L-α-aspartyl]-L-phenylalanine 1-methyl ester or a salt thereof in an amount effective to sweeten said frosting.

16. A method of sweetening a bakery filling by including in said bakery filling a sugar co-crystallized sweetener composition comprising sugar and N-[N-(3,3-dimethylbutyl)-L-α-aspartyl]-L-phenylalanine 1-methyl ester or a salt thereof in an amount effective to sweeten said bakery filling.

17. The method according to claim 16, wherein said bakery filling is a low or neutral pH filling, a high, medium or low solids filling, a fruit or milk based filling, a hot or cold make-up filling and a non-fat to full-fat filling.

18. A method of sweetening a candy or chewing gum by including in said candy or chewing gum a sugar co-crystallized sweetener composition comprising sugar and N-[N-(3,3-dimethylbutyl)-L-α-aspartyl]-L-phenylalanine 1-methyl ester or a salt thereof in an amount effective to sweeten said candy or chewing gum.

19. A method of sweetening a table-top sweetener by including in said table-top sweetener a sugar co-crystallized sweetener composition comprising sugar and N-[N-(3,3-dimethylbutyl)-L-α-aspartyl]-L-phenylalanine 1-methyl ester or a salt thereof in an amount effective to sweeten said table-top sweetener.

* * * * *

UNITED STATES PATENT AND TRADEMARK OFFICE
CERTIFICATE OF CORRECTION

PATENT NO. : 6,214,402 B1
DATED : April 10, 2001
INVENTOR(S) : Jim Fotos et al.

It is certified that error appears in the above-identified patent and that said Letters Patent is hereby corrected as shown below:

<u>Title page,</u>
Item [54], "-LαASPARTYL]-" should read -- L-α-ASPARTYL] --.

<u>Column 1,</u>
Line 2, "-L" should read -- L --; and
Line 3, "αASPARTYL]-" should read -- α-ASPARTYL]- --.

Signed and Sealed this

Eleventh Day of June, 2002

Attest:

Attesting Officer

JAMES E. ROGAN
Director of the United States Patent and Trademark Office